United States Patent [19]

Bisconte

[11] Patent Number: 5,321,545
[45] Date of Patent: Jun. 14, 1994

[54] MICROSCOPE STAGE FOR RAPID AND INDEXED ANALYSIS OF FILTERS AND OTHER MEDIA CARRYING MULTIPLE SAMPLES, AND A METHOD OF ANALYZING SUCH SAMPLES USING SAID STAGE

[75] Inventor: Jean-Claude Bisconte, Briis-sous-Forges, France

[73] Assignee: Biocom S.A., Les Ulis, France

[21] Appl. No.: 678,257

[22] PCT Filed: Nov. 20, 1989

[86] PCT No.: PCT/FR89/00545

§ 371 Date: May 31, 1991

§ 102(e) Date: May 31, 1991

[87] PCT Pub. No.: WO90/04802

PCT Pub. Date: May 3, 1990

[30] Foreign Application Priority Data

Oct. 21, 1988 [FR] France ................................ 88 13805

[51] Int. Cl.⁵ .................................................. G02B 21/26
[52] U.S. Cl. ...................................... 359/391; 359/396; 359/397
[58] Field of Search ........................ 359/391-398; 269/21, 22; 422/66, 73, 102; 435/300, 313; 248/362

[56] References Cited

U.S. PATENT DOCUMENTS

| | | | |
|---|---|---|---|
| 3,549,232 | 12/1970 | Hugle | 359/394 |
| 3,731,377 | 5/1973 | Muckelroy | 29/834 |
| 3,826,558 | 7/1974 | Rasberry et al. | 359/393 |
| 4,526,445 | 7/1985 | Wogoman | 359/398 |
| 4,538,885 | 9/1985 | Graham et al. | 359/391 |
| 4,807,984 | 2/1989 | Kurimura et al. | 359/393 |
| 4,946,266 | 8/1990 | Kraft et al. | 359/391 |
| 4,981,345 | 1/1991 | Berry et al. | 359/391 |

FOREIGN PATENT DOCUMENTS

| | | | |
|---|---|---|---|
| 1013563 | 7/1977 | Canada | 359/396 |
| 2122375 | 1/1984 | European Pat. Off. | 359/391 |
| 229581 | 7/1987 | European Pat. Off. | |
| 3427213 | 1/1986 | Fed. Rep. of Germany | |
| 2565350 | 6/1985 | France | |
| 1297880 | 11/1972 | United Kingdom | |

OTHER PUBLICATIONS

"Work Holder and Alignment Device", Lanpdon et al., IBM Technical Disclosure Bulletin, vol. 5, No. 9, Feb. 1963, pp. 7-8.

Primary Examiner—Bruce Y. Arnold
Assistant Examiner—Thong Nguyen
Attorney, Agent, or Firm—Bell, Seltzer, Park & Gibson

[57] ABSTRACT

A stage (1) for fixing at least one porous or non-porous medium (27) that carries one or more samples to be observed and to be analyzed by means of a microscope. The stage includes a hole (10) for receiving a plate (20; 28) for supporting the medium (27) and thus for observing the samples carried thereby. The stage is designed for pressing the medium (27) against the support plate (20; 28) by suction. The invention is applicable to the biological industry for rapid and indexed analysis under a microscope of filters and other media carrying multiple samples.

16 Claims, 2 Drawing Sheets

MICROSCOPE STAGE FOR RAPID AND INDEXED ANALYSIS OF FILTERS AND OTHER MEDIA CARRYING MULTIPLE SAMPLES, AND A METHOD OF ANALYZING SUCH SAMPLES USING SAID STAGE

BACKGROUND OF THE INVENTION

1. Field of the Invention

The present invention relates to a stage for holding porous media (filters) or non-porous media, that are flexible or rigid, and that carry multiple samples which may be biological or otherwise, and also to a method of analyzing said samples using the above-mentioned stage. The stage is suitable for placing beneath an optical microscope and may constitute an over-stage, or else it may replace the conventional stage. The stage of the invention is particularly suitable for analyzing samples rapidly, in particular by making use of automatic image analysis by computer.

2. Description of the Prior Art

It is recalled that in microscopy the object rests on a glass slide and, in general, it is covered by a glass cover-slip. When analyzing bacteria on a filter, this additional medium is naturally present, given that the only possible technique presently known for ensuring that the filter is properly plane is to mount it between a slide and a cover-slip.

Conventionally, a microscope stage includes a fixing plane which is fixed to a focusing rack. The plane of the stage moves in the Y direction and the slide is held by a vice that is movable in the X direction. The slide is placed against the stage and a spring jaw is pressed laterally against the slide. In practice, this system suffers from two defects:

1) the glass slide may be at a slight angle relative to the plane of the stage; and 2) the lateral stress exerted by the spring may curve the slide slightly.

At high magnification, and when performing X and Y displacement, it thus becomes essential to keep on readjusting the focus, to such an extent that a microscope operator generally works with one hand constantly active on the micrometer screw.

The ever increasing use of image-analyzing computers coupled to microscopes has led to X-Y stages being used that are driven by stepper motors. On the more sophisticated models, a special over-stage stresses the slide better.

Regardless of whether conventional analysis or automatic image analysis is being performed, the system includes a glass slide (with the commonest size being 75 mm×25 mm×1.2 mm) that will never be accurately plane given that the slide is very thin (1.2 mm) and very long (75 mm). In addition, slides are cheap consumable objects and they are not required to have very special optical properties.

It should be observed that the thinness of the slide is desirable for optical reasons. In conventional microscope applications, light arrives from below (transmitted light) via a condenser. To ensure that the illumination is intense and uniform, it is necessary to bring the condenser as close to the object as the objective lens.

This is not possible at very high magnification. An objective lens having a magnification of 100 times (giving a total magnification of 2000) is disposed at a distance of about 0.2 mm from the object (which leaves only just enough room for the cover-slip over the object).

Naturally, when using epifluorescence, there is no need for a condenser since the illumination arrives via the objective lens.

With filters, mounting a filter between a slide and a cover-slip is the only available technique for making the filter properly plane.

Filtration is being used more and more for analyzing particles contained in gases and liquids. These particles are varied in nature, being biological, mineral, metallic, etc. . . . One example is separating and counting bacteria in milk (using filters known under trade names "NUCLEOPORE", "MULLIPORE", etc.).

It should also be recalled that a liquid mounting medium is required, constituting either by oil, or by a viscous medium (Canada balsam) or else by a medium that sets over time.

The corresponding operations are relatively difficult and not very compatible with notions of high analysis throughput.

In addition, it is very difficult to obtain an accurately plane preparation. The filter cannot be pressed down accurately and the inevitable differences in the thickness of the above-mentioned mounting liquid cause the cover-slip itself to be deformed (which is not very serious if immersion oil is interposed between the objective lens and the cover-slip).

It should therefore be observed that it is theoretically not possible merely to place the filter on a conventional glass slide for direct observation while dry. The undulations of the filter would be too big. However, there would be immense advantages in terms of simplicity and said if such observation were possible.

Thus, it may be observed that automatic image analysis which gives the best performance finds its performance degraded by the unsuitability of the methods of preparing and observing the sample. J-C. BISCONTE has described elsewhere a method making use of transparent films for continuous observation by image analysis (cf. French patent FR-2 565 350 and the patent issued on Euro-PCT patent application WO 85/05563).

For each slide, it is necessary to initialize image analysis, in particular to verify focusing.

This focusing problem is the most difficult part of analyzing small particles, and in particular for analyzing bacteria.

In this context, it may be recalled that bacteria may sometimes measure less than one micron, and that under the best observation conditions, the depth of field is about half a micron. Thus, a defect in planeness of about one micron suffices to take bacteria completely out of focus, and therefore make them unsuitable for automatic analysis.

It is possible in image analysis to perform an automatic search for the best focus, however this process takes time. It requires 3 to 10 positions of stage height to be tested (in increments of 0.25 microns) in order to find the best adjustment (greatest degree of sharpness in the observed objects).

If the surface of the filter is subject to large fluctuations in planeness, e.g. of about 50 microns, then the image analysis faced with an empty field must be capable of deciding whether the field really is free from bacteria or whether the field is badly out of focus. It is quite normal to spend 10 to 20 seconds analyzing such a field! . . .

Unfortunately, such fields cannot be "skipped" since that runs the risk of obtaining completely erroneous results.

Patent application GB-2 141 254 (Miles) describes a device for holding an object to be observed stably in position on an observation window. To this end, that device comprises in combination:
- a plate having mutually parallel main faces and an optical observation window of transparent material centrally disposed in a through opening therein;
- an annular suction gap surrounding the optical observation window; and
- a duct connecting the annular suction gap to a vacuum source (or source of reduced pressure).

More precisely, Miles sets out essentially to replace the conventional slide carrier of a microscope which is unsuitable for supporting a flexible film, and also to avoid touching the top main face of the film so as to prevent any contamination or scratching thereof, and as a result Miles should be considered as constituting the technological background of the present invention while also illustrating the closest state of the art to the invention.

An object of the present invention is thus to provide a stage for holding porous media (filters) or non-porous media, that are flexible or rigid, and that carry samples which my be biological or otherwise, the stage satisfying practical requirements better than a conventional stage, and in particular:

1) it makes it possible to obtain a medium for analysis that is accurately plane;
2) it is particularly suitable for automatically and rapidly holding one or more samples in indexed manner for easy analysis (disposed on the same medium and always presented in the same X, Y, and Z manner) for the purpose of automatic image analysis by computer or for the purpose of manual analysis;
3) it is also suitable for automatically searching for the best focus;
4) it is compatible with observation both by transmission and by epifluorescence;
5) it enables the medium to be observed directly without a cover-slip, thereby making it possible to use microscope objective lenses having very short focal lengths, thus obtaining better performance;
6) it is compatible with dry observation and with observation under an immersion oil; and
7) while being particularly adapted to optical microscopy, it may also be applied to electron microscopy or to other means of observation.

A preferred application of the stage of the invention is constituted by counting bacteria on "NU-CLEOPORE" type microporous filters.

SUMMARY OF THE INVENTION

The present invention provides a stage for fixing at least one porous or non-porous medium that is flexible or rigid and that carries one or more samples which are biological or otherwise to be observed and to be analyzed, the stage including a hole in which a medium support plate is disposed, and thus enabling the samples carried thereby to be observed, and also means for pressing the medium onto the support plate by suction, the stage being characterized in that it further includes means for automatically indexing the medium and thus said samples to be analyzed, said means comprising a card including an opening corresponding to the hole in the stage, together with means for centering the card on the stage, i.e. position indexing means, said medium being designed to be fixed to one of the main faces of the card around an annular zone of the card delimiting the above-mentioned opening.

In accordance with the invention, the card position indexing means comprise at least two perforations for receiving two corresponding centering studs carried by the stage.

In a preferred embodiment of the stage of the invention, including means for pressing the medium against the support plate that comprise the following in combination:
- an airtight annular gap provided at least around the plate and delimited between said plate, the stage, and at least an annular peripheral portion of the medium projecting beyond the plate;
- a device for applying suction to at least said annular peripheral portion of the medium to be analyzed, by creating a vacuum; and
- at least one airtight channel provided in the stage and putting the airtight suction gap into communication with the device for creating a vacuum;
- the plate is fixed to a radially inner end of an annular seat projecting from a portion of the wall delimiting the hole through the stage, the observation face of the plate against which the medium is pressed being at the same level as the top face of the stage when said plate is disposed in said hole, said plate having a radially outer surface portion spaced apart from the wall of the hole by said seat such that the airtight suction gap is delimited between: said radially outer surface portion of the plate, a surface portion of the seat on which the plate is fixed, said portion of the wall delimiting the hole through the stage, and said annular peripheral portion of the medium overlying in airtight manner the gap between the plate and the wall of the hole through the stage, the channel connecting the device for creating a vacuum to the airtight gap for applying suction to at least the annular peripheral portion of the medium being constituted by at least one blind groove formed in the stage and including a seat for receiving an airtight closure strip (for this suction groove) provided with a suction orifice for coupling to the above-mentioned device for creating a vacuum.

In an advantageous variant of the above-mentioned embodiment, said means for pressing the medium against the observation plate comprise, in combination:
- an airtight annular gap provided at least around the plate and delimited between said plate, the stage, and at least an annular peripheral portion of the medium projecting beyond the plate; and
- a device for applying suction to at least said peripheral zone of the medium to be analyzed by establishing an electromagnetic field suitable for magnetizing at least said annular peripheral portion of the medium, which is fitted with or made of an annular band of ferromagnetic material.

In another advantageous variant of the above-mentioned embodiment, the medium pressing means comprise:
- a device for applying suction to at least an annular peripheral zone of the medium to be analyzed by establishing a vacuum, which device is in communication with said peripheral zone of the medium, the observation plate being porous at least in a portion corresponding to said peripheral zone, said peripheral zone of the medium being pressed against the observation plate.

In an advantageous disposition of these two variant embodiments, the plate is fixed to a radially inner end of an annular seat projecting from a wall portion delimiting the hole through the stage, the observation face of the plate against which the medium is pressed being at substantially the same level as the top face of the stage when said plate is disposed in the above-mentioned hole, said plate having a radially outer surface portion spaced apart from the wall of the hole by said seat in such a manner that the airtight suction gap is delimited between: said radially outer surface portion of the plate, a surface portion of the seat on which the plate is fixed, said portion of the wall delimiting the hole through the stage, and said annular peripheral portion of the medium overlying in airtight manner the gap between the plate and the wall of the hole through the stage, the channel connecting the device for creating a vacuum to the airtight gap for applying suction to at least the annular peripheral portion of the medium being constituted by at least one blind groove formed in the stage and including a seat for receiving an airtight closure strip provided with a suction orifice for coupling to the above-mentioned device for creating a vacuum.

In a preferred disposition of the above embodiment and of its variants mentioned above, the plate includes a grid of microgrooves disposed in its observation surface in such a manner as to distribute the suction created in the above-mentioned suction gap also to the bottom face of the medium around each of the microsquares (or micropanes) in the medium, with the observation face of the support plate, i.e. its top main face, being subdivided by the grid of microgrooves into corresponding microsquares or micropanes, thereby pressing down the medium even better during suction.

In addition to the preceding dispositions, the invention further includes other dispositions which appear from the following description.

BRIEF DESCRIPTION OF THE DRAWINGS

The invention will be better understood from the following additional description which refers to the accompanying drawings, in which.

It should nevertheless be understood that these drawings and the corresponding portions of the description are given purely to illustrate the subject matter of the invention, and that they do not constitute any kind of limitation thereon.

DESCRIPTION OF THE ILLUSTRATED EMBODIMENTS

Figure 1:
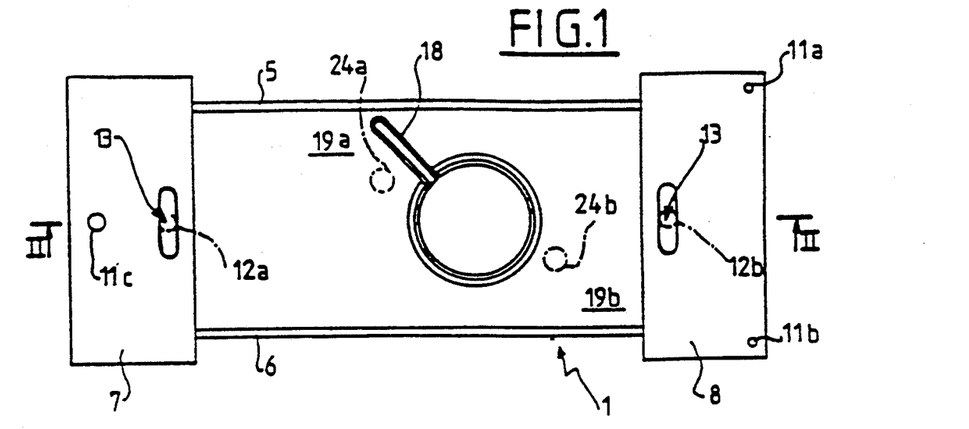
FIG. 1 is a plan view of a stage of the invention.
Figure 2:
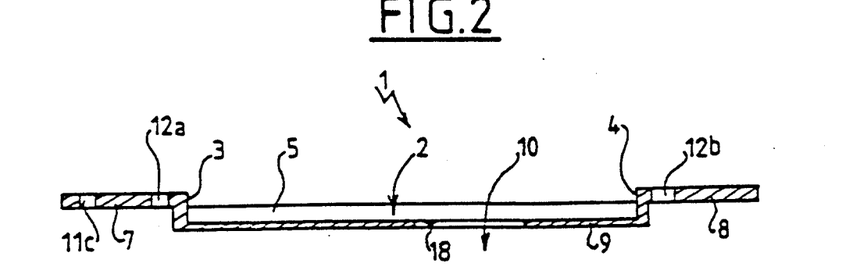
FIG. 2 is a section view of the stage shown in FIG. 1, on line II—II.

The stage 1 of the invention as shown in FIGS. 1 and 2 is rectangular in shape and is made of light alloy. A solid plate of this alloy is machined so as to form a kind of trough 2 in the top thereof delimited by two transverse shoulders or ribs 3 and 4 and two longitudinal ribs 5 and 6. The trough shape serves to prevent liquid escaping when performing immersion observation. The stage 1 may be used as an overstage for placing on a conventional microscope stage, or it may take the place thereof.

The ribs 3 and 4 extend higher than the ribs 5 and 6 and beyond the ends thereof, and they also extend over a width greater than the distance between the ribs 5 and 6. Two fins 7 and 8 project outwards from the top edges of the ribs 3 and 4 and contribute to imparting a high degree of rigidity to the stage 1.

In the example shown, the thickness of these fins is substantially equal to the difference in height between the ribs 3, 4 and the ribs 5, 6.

A hole 10 is made through the bottom 9 of the trough 2. When the stage 1 is used as an over-stage, this hole 10 should be aligned with the conventional stage per se of a microscope (not shown) with the stage 1 bearing against the conventional stage at three points such as those defined by references 11a, 11b, and 11c. These points are constituted by bores (with at least the bores 11a and 11b being tapped) to enable the parallelism of the stage 1 to be adjusted relative to a support plane by means of micrometer screws (not shown, and more precisely it is the parallelism of the glass plate described below which is adjusted).

Oblong slots 12a and 12b receive spring type clamping members 13 capable of rotating through 90° and fixed to the above-mentioned support plane (not shown in FIGS. 1 and 2; with the clamping members also being omitted from FIG. 2). In the unlocked position, the clamping members 13 release the stage 1, while in the locking position they serve to fix the stage firmly against the stage of the microscope by interacting with the walls of the oblong slots 12a and 12b. More precisely, in the locking position, the springs of the clamping members urge the stage 1 against its three above-mentioned fixing points 11a, 11b, and 11c.

In accordance with the invention, a glass plate 20 (see FIG. 3) is placed in the hole 10 in the stage 1 and bears against a seat 15 projecting radially into the hole 10 from the wall 14 delimiting the hole and defined on a bottom shoulder or step 16. More precisely, the seat is constituted by the chamfered end 16a of the shoulder 16 on which it is fixed by gluing or any other means, e.g. by screwing. In this way, an annular gap 17 (e.g. about 1 mm wide) extends between the glass plate 20 and the wall 14 of the hole 10, which gap is intended to he covered by the medium 27 to be analyzed which covers the gap 17 in airtight manner by means of a peripheral annular portion projecting beyond the plate 20 whose observation face 28 (i.e. the face against which the medium 27 bears) is in alignment with the top face 29 of the bottom 9 of the stage 1. This gap 17 is thus delimited between: a radially outer surface portion 30 of the plate 20; a surface portion 31 of the fixing seat 15 for the plate; a portion of the wall 14 delimiting the hole 10 in the stage 1; and the annular peripheral zone 27a of the medium 27 which overlies in airtight manner the gap 17 between the plate 20 and the wall 14 of the hole 10.

A groove 18 is formed in the bottom 9 of the stage 1, which groove is closed at one end 19a and opens out at its opposite end 19b into the annular gap 17 (in FIG. 1, the groove is shown as extending on an extension of a diameter of the hole 10). A seat 21 is formed in the groove 18 for receiving an airtight closure strip 22 of the groove, such as the strip shown in FIG. 5, thereby providing an airtight channel (naturally the airtight channel could be made in some other way). The strip 22 is provided with an orifice 23 constituting a suction orifice for connection via a suction endpiece to a device for creating a vacuum.

Figure 5:
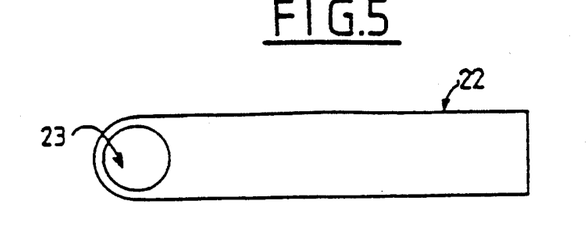
FIG. 5 is a plan view of an airtight closure strip for closing the groove visible in FIGS. 1 and 4, thereby transforming the groove into an airtight suction channel.

The closure plate 22 is glued to its seat 21 (although other fixing methods could be used, in particular it could be screwed in place using microscrews fitted with microsealing rings).

Figure 3:
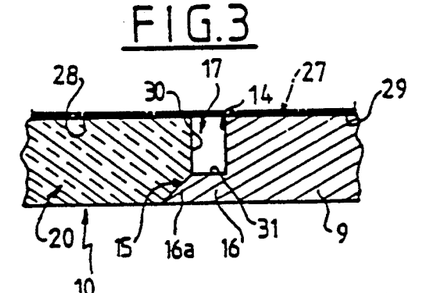
FIG. 3 shows a detail of FIG. 2 on a larger scale applicable to the hole in the stage for receiving a support plate for a medium having samples to be analyzed, showing the disposition of the gap in which the vacuum is created as required for pressing the medium onto the plate by suction.
Figure 4:
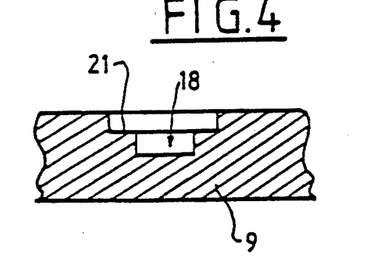
FIG. 4 shows a suction groove on a larger scale and in section, the groove is blind at one end and serves to put said suction gap into communication via an orifice (provided in the strip of FIG. 5) with a suction device.

By connecting the orifice 23 via said coupling endpiece to a device for creating a vacuum (not shown), it is possible to evacuate the annular gap 17 surrounding the glass plate 20, which plate is rectified to ensure that the medium 27 is very plane.

The suction applied to the medium in this way causes it to be pressed firmly and accurately against the glass plate under the action of the peripheral zone 27a of the medium 27 being permanently tensioned.

Suction may be applied to transparent non-porous media which may thus constitute an advantageous replacement for the glass plate 20. With such media, the suction and the resulting pressing provide planeness of a quality that is at least equivalent to that of a conventional glass slide.

If provided with a removable frame having inside dimensions equivalent to those of a conventional glass slide, the stage may also be used for conventional observation. The frame is designed to close all of the suction zones apart from the evacuated zone, in which the conventional glass slide finds itself pressed down firmly without deformation. Another consequence of the medium being accurately pressed against the glass plate is that it is possible to observe the medium without an object cover-slip, i.e. without using the component that constitutes the only means available in the prior art for obtaining a medium of satisfactory planeness. By omitting the object cover-slip, it is possible to make use of microscope objective lenses having very short focal lengths, thereby obtaining better performance.

In addition, by eliminating undulations in the medium by putting it under tension, it is possible to observe a filter directly while dry, thereby obtaining the advantages of simplicity and rapidity as mentioned above.

In addition, because of the excellent tensioning of the medium (adjustable by varying the amount of suction), and thus the elimination of planeness defects, it is possible to apply automatic focus searching effectively while using image analysis to observe samples carried by a medium. Such planeness eliminates the above-mentioned focusing errors that are unacceptable when attempting to perform automatic focusing on a medium for which the problem of fluctuations in planeness remains to be solved.

In addition, it is also possible to take account of defects that may arise in the planeness of the plate itself: to this end, the memory of a computer serving, in particular, to control automatic focusing by image analysis can store information concerning plate defects as a function of position, and can thus apply corrections during analysis before inputting the image of a new field.

Figure 6:
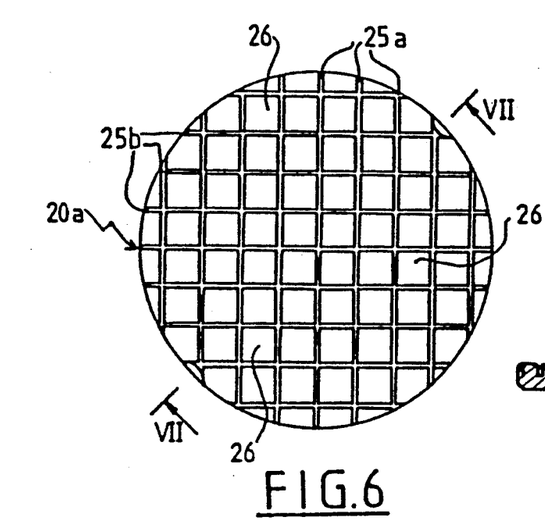
FIG. 6 is a plan view of a variant embodiment of the plate shown in FIG. 3.
Figure 7:
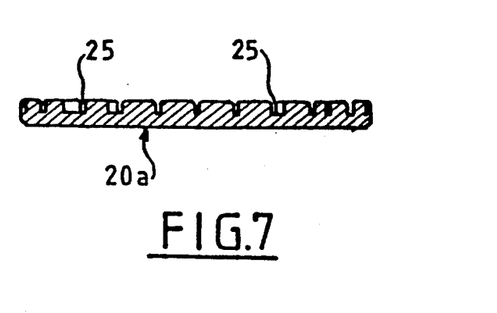
FIG. 7 is a diametral section taken along line VII—VII of the plate shown in FIG. 6.

In the context of the present invention, it is also possible to further improve the planeness of the medium relative to the glass plate against which it is pressed by forming two mutually perpendicular sets of microgrooves 25a and 25b in the observation face of the plate, e.g. the plate 20a shown in FIG. 6. This provides a grid which communicates with the annular gap 17 and thus with the suction groove 18 and the suction orifice 23. In this manner, a medium overlying a gridded glass plate 20a is pressed thereagainst not only because the medium is tensioned by the suction applied to the annular peripheral zone thereof that overlies the above-mentioned annular suction gap 17, but also because of each of the small internal squares 26 oh the support as delimited by four microgrooves 25 is individually tensioned, thereby pressing the medium better against the glass plate.

The microgrooves 25 are disposed in such a manner that the resulting grid is compatible with the positions of the samples to be observed on the filter, i.e. so that each sample is framed by four microgrooves, thereby enabling the various samples to be analyzed sequentially.

It should also be added that the stage 1 of the invention is compatible not only with observation by epifluorescence, but also with conventional observation by transmission, i.e. by light transmitted using a condenser, and that this is achieved by using transparent media on the stage 1. Although it is true that the 2 mm to 3 mm thickness of the glass plate provided in the stage is greater than the thickness of a conventional slide, thereby preventing the condenser from coming as close to the medium as it does in a conventional microscope, it should nevertheless be observed that condensers are now available having longer focal lengths and providing excellent results.

Regardless of the microscope technique used and thus of the microscope adopted, it is clear that a microscope fitted with a stage of the invention, and co-operating with a camera, makes it possible for samples (cells, bacteria, etc.) carried by the medium to be analyzed (observed and counted) by means of image analysis software loaded into a computer for controlling the microscopic observation, and in particular for performing automatic focusing and for counting particles.

As a function of the level of illumination, the above-mentioned image analysis software determines the number of fluorescent objects in the image seen by the camera.

From the above, it is clear that the present invention makes it possible to implement an original analysis method observation and counting) applicable to one or more samples carried on a medium, by means of a microscope connected to a camera which is connected in turn to an image analyzer under the control of a computer having image analysis software loaded therein, which method has the characteristic (that is essential for proper observation and counting) constituted by a prior operation of pressing the medium to be analyzed against the plate carried by the stage of the invention so as to eliminate fluctuations in planeness of the medium and so as to make automatic searching for the best focus by the above-mentioned image analyzer really effective.

On the basis of the above dispositions, a preferred way of pressing the medium against the plate consists in applying suction to at least one peripheral annular zone thereof by establishing an airtight gap around the plate against which the medium is pressed, which gap is suitable for being put into communication with a device for applying suction, at least to said peripheral zone.

In addition, the Applicant has designed a parallel filter apparatus for filtering a plurality. of samples with clogging being monitored automatically and with the filters used being indexed, which apparatus constitutes the subject matter of a co-pending patent application. Filters carrying a plurality of samples to be analyzed located in a multiplicity of separate zones on the same filter can be analyzed effectively by means of the stage and by applying the analysis method of the invention.

Figure 8:
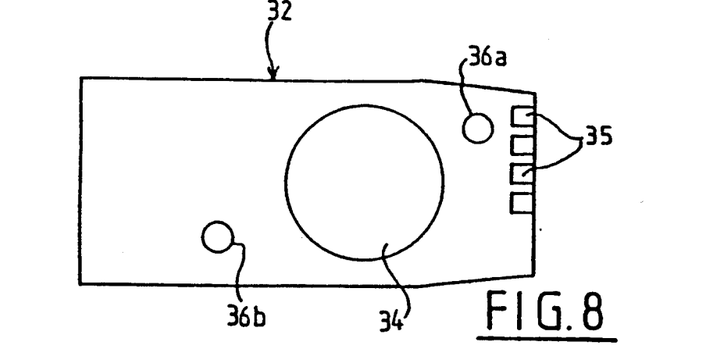
FIGS. 8 and 9 are respectively a view from above and a view from below of a medium-carrying card for co-operating, when appropriate, with the stage of the invention.
Figures 9, 10:
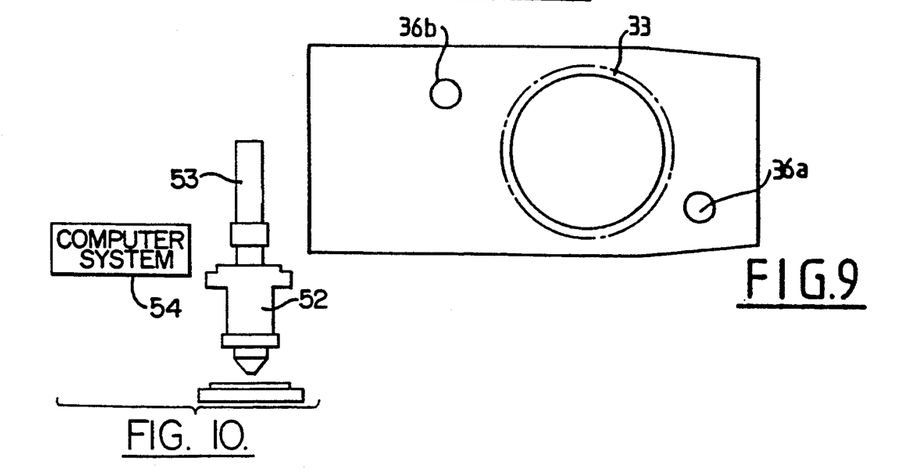
FIG. 10 is a schematic view showing a microscope equipped with a stage of the invention.

In addition, the stage of the invention advantageously cooperates with a medium-carrying card which is preferably made of flexible plastic material and which is of the type shown and described in the above-mentioned co-pending patent application. For reasons of convenience, this card is also shown in FIGS. 8 and 9 of the drawings accompanying the present application, in which it is given the reference 32.

In this case, the medium to be analyzed is glued to the card 32 in an annular zone referenced 33 which delimits a circular opening 34 corresponding to the hole 10 in the stage 1 of the invention.

When such a card is used, it advantageously co-operates with a keying system, either by providing keying notches or perforations on the card (as referenced 35 in FIG. 8) or else, more simply, by cutting out or perforating the periphery of the medium to be analyzed. In addition, the card may advantageously be centered on the stage of the invention, in particular by means of two centering studs such as those shown in dot-dashed lines in FIG. 1 and given references 24a and 24b, and intended to co-operate with two centering holes or perforations 36a and 36b formed through the card 32. Once centered on the stage 1, the card constitutes original means for indexing the medium and thus the sample(s) carried thereon, and it is also pressed against the stage by the means used for pressing the medium thereagainst.

The present invention thus provides a stage which simultaneously satisfies two objectives, namely making it possible at the same time:

i) to achieve accurate pressing by the grid for distributing the suction established in the annular suction gap over the bottom face of the filter and around each of the microsquares (or micropanes) 26 of the filter by virtue of the observation face 20a (i.e. the top main face) of the support plate being subdivided by a grid of microgrooves, thus pressing of the filter better against the plate during suction; and ii) to obtain a reference surface which is stable over time, which is perfectly plane (to an accuracy of 0.2 $\mu$m) and which is perfectly horizontal (with an accuracy of 1 $\mu$m to 2 $\mu$m), while presenting the following advantages, separately or in combination:

1) the medium is pressed down exceptionally quickly, even with observation plates of relatively large diameter;

2) very accurate automatic indexing;

3) focusing is stable, reproducible, and correctable by computer;

4) observation can be performed dry or under oil; and 5) two types of illumination may be used: from above (epi-illumination) or from below (trans-illumination).

As follows from the above, the invention is not limited in any way to the implementations and embodiments thereof that are described explicitly. On the contrary, the invention extends to any variant that may occur to the person skilled in the art without going beyond the context or the scope of the present invention. In particular, it is clear that the airtight suction gap created around the glass plate and coinciding at least with the annular peripheral zone of the medium to be analyzed may be put into communication with the device for establishing a vacuum not only by means of a single groove such as the groove 18 described, but also by any other equivalent means, for example by means of a plurality of airtight grooves disposed in a star configuration around the hole through the stage of the invention, or else by means of a porous glass.

The glass itself may be replaced by different materials such as metals or synthetic materials (plastics), which can be advantageous for analysis by epifluorescence, i.e. when there is no need to transmit illumination from a condenser.

When a porous plate is used, it may be porous throughout its bulk, or solely in an annular peripheral portion corresponding to the annular peripheral zone of the medium and applied against the observation plate, with suction being applied to the medium by establishing a vacuum by means of an appropriate device communicating with said peripheral zone of the medium.

Similarly, it is possible to create suction in at least one annular peripheral zone of a medium to be analyzed, thereby pressing the medium down, by using a device for establishing an electromagnetic field which acts at least on said peripheral zone of the medium, which zone should then be fitted with or made of an annular band of ferromagnetic material capable of being magnetized and thus "sucked" (attracted) by the magnetic field.

In each case suction, in particular of the peripheral zone of the medium to be analyzed, subjects the medium to continuous peripheral tension which causes it to be pressed effectively against the observation plate.

It should also be observed that the observation plate may even be constituted by a conventional observation slide. In this case (this disposition is not shown in the drawings), the stage of the invention is advantageously fitted with an airtight film provided with a central observation window for centering relative to the above-mentioned hole (10) of the stage, while being smaller than said hole (10), said observation slide being fixed on an annular zone of the film which centrally delimits the observation window thereof, such that the above-mentioned slide is pressed against the stage when suction is applied.

In addition, it is also advantageous for obtaining even more effective pressing to make the microgrooves of the grid for distributing suction to the bottom main face of the medium with rounded edges, and also to make them with a cross-section whose profile is likewise rounded.

In addition, it should be understood that when the stage of the invention is used as an over-stage for mounting on a microscope stage which maybe conventional or otherwise (instead of being used as a replacement for a microscope stage, conventional or otherwise), then the stage of the invention is not provided with any degree of freedom of its own, other than being removable, with the stage that carries it being motorized and capable of performing X, Y, and Z displacements.

It is also very advantageous to cause a microscope fitted with the stage of the invention to co-operate with a system for automatic focusing by video image analysis under computer control, thereby making it possible to store defects in the planeness of the medium in memory by detecting the real altitudes of the observation surface thereon relative to the reference surface, such that each time the system moves, it automatically makes a correction for altitude (under the control of a suitable program) so as to adapt to small random variations in altitude.

I claim:

1. A stage for fixing at least one medium that carries one or more samples to be observed and to be analyzed by means of a microscope, the stage including a hole, a support plate received in said hole for supporting the medium and thus for enabling the sample carried thereby to be observed, means for pressing the medium against the support plate by suction, means for indexing the medium and thus said sample to be analyzed, said indexing means comprising a card including an opening corresponding to the hole through the stage, said medium being fixed to one of the main faces of said card over an annular zone thereof delimiting said opening.

2. A stage according to claim 1 characterized in that the means for indexing the medium include at least two perforations for receiving two corresponding centering studs carried by the stage.

3. A stage according to claim 1, characterized in that sad means for pressing the medium against the support plate comprise, in combination:
   an airtight annular gap provided at least around the plate and delimited between said plate, the stage, and at least an annular peripheral portion of the medium projecting beyond the plate; and
   a device for applying suction to at least said annular peripheral portion of the medium to be analyzed by establishing an electromagnetic field suitable for magnetizing at least said annular peripheral portion of the medium, which is fitted with or made of an annular band of ferromagnetic material.

4. A stage according to claim 3, characterized in that the plate is fixed to a radially inner end of an annular seat projecting from a wall portion delimiting the hole through the stage, the observation face of the plate against which the medium is pressed being at substantially the same level as the top face of the stage when said plate is disposed in hole, said plate having a radially outer surface portion spaced apart from the wall of the hole by said seat in such a manner that the airtight suction gap is delimited between: said radially outer surface portion of the plate, a surface portion of the seat on which the plate is fixed, said portion of the wall delimiting the hole through the stage, and said annular peripheral portion of the medium overlying in airtight manner the gap between the plate and the wall of the hole through the stage, the channel connecting the device for creating a vacuum to the airtight gap for applying suction to at least the annular peripheral portion of the medium being constituted by at least one blind groove formed in the stage and including a seat for receiving an airtight closure strip provided with a suction orifice for coupling to said device for creating a vacuum.

5. A stage according to claim 1, characterized in that the means for pressing down the medium comprise:
   a device for applying suction to at least an annular peripheral zone of the medium by establishing a vacuum, which device is in communication with said peripheral zone of the medium, the support plate being porous at least in a portion corresponding to said peripheral zone, said peripheral zone of the medium being pressed against the support plate.

6. A stage according to claim 1, wherein said means for pressing the medium against the support plate comprises in combination:
   an airtight annular gap provided at least around the plate and delimited between said plate, the stage, and at least an annular peripheral portion of the medium projecting beyond the plate;
   a device for applying suction to at least said annular peripheral portion of the medium by creating a vacuum;
   at least one airtight channel provided in the stage and putting the airtight suction gap into communication with the device for creating a vacuum;
   the stage being characterized in that the plate is fixed to a radially inner end of an annular seat projecting from a portion of the wall delimiting the hole through the stage, the observation face of the plate against which the medium is pressed being at substantially the same level as the top face of the stage when said plate is disposed in said hole, said plate having a radially outer surface portion spaced apart from the wall of the hole by said seat such that the airtight suction gap is delimited between: said radially outer surface portion of the plate, a surface portion of the seat on which the plate is fixed, said portion of the wall delimiting the hole through the stage, and said annular peripheral portion of the medium overlying in airtight manner the gap between the plate and the wall of the hole through the stage, the channel connecting the device for creating a vacuum to the airtight gap for applying suction to at least the annular peripheral portion of the medium being constituted by at least one blind groove formed in the stage and including a seat for receiving an airtight closure strip provided with a suction orifice for coupling to said device for creating a vacuum.

7. A stage according to claim 6, characterized in that the support plate includes a grid of microgrooves disposed in its top main surface to distribute the suction created in the suction gap also to the bottom face of the medium, with the top main face of the support plate being subdivided by the grid of microgrooves into corresponding microsquares or micropanes, thereby pressing down the medium even better during suction.

8. A stage according to claim 1, characterized in that it is in the form of a trough.

9. A stage according to claim 8, characterized in that the trough is substantially rectangular and is delimited by transverse ribs and longitudinal ribs, and in that the transverse ribs are fitted with reinforcing fins also serving to enable the stage to co-operate with means for fixing the stage on a support plane.

10. A stage according to claim 1, characterized in that the plate is made of a material selected from the group consisting of glass materials, metal materials, and plastics materials.

11. A microscope fitted with a stage according to claim 1.

12. A microscope according to claim 11, characterized in that it co-operates with a computer controlled system for automatic focusing by analyzing a video image.

13. A stage for fixing at least one medium that carries one or more samples to be observed and to be analyzed by means of a microscope, said stage including a hole, a support plate received in said hole for supporting the medium and thus for observing the sample carried thereby, said support plate including microgrooves disposed in its top main surface to form a grid, and means for applying suction to the microgrooves so as to thereby press the medium against the support plate, with the grid of microgrooves serving for distributing the suction to the bottom face of the medium around each of the microsquares subdivided by the grid of microgrooves, thereby pressing down the medium even better during suction.

14. A stage according to claim 13, wherein said support plate disposed on the top of said stage is transparent.

15. A stage for fixing at least one medium that carries one or more samples to be observed and to be analyzed by means of a microscope, said stage including a hole, a support plate received in said hole for supporting the medium and thus for observing the sample carried thereby, means for pressing the medium against the support plate by suction, means for indexing the medium and thus said sample to be analyzed, said means for indexing the medium comprising a card which includes an opening corresponding to the hole through the stage, said medium being designed to be fixed to one of the main faces of the card over an annular zone thereof delimiting the above-mentioned opening, said support plate including microgrooves disposed in its top main surface to form a grid for distributing the suction to the bottom face of the medium around each of the microsquares subdivided by the grid of microgrooves, thereby pressing down the medium even better during suction.

16. A stage for fixing at least one film that carries one or more samples to be observed and to be analyzed by means of a microscope, comprising a support plate for supporting the film and for observing the samples carried thereby, said support plate having a grid of microgrooves disposed on its top main surface and further comprising a vacuum source connected to said grid of microgrooves to distribute suction to the bottom face of those portions of the film positioned on the top main surface of the support plate that lie directly above each microgroove.

* * * * *

UNITED STATES PATENT AND TRADEMARK OFFICE
CERTIFICATE OF CORRECTION

PATENT NO. : 5,321,545

DATED : June 14, 1994

INVENTOR(S) : Jean-Claude Bisconte

It is certified that error appears in the above-identified patent and that said Letters Patent is hereby corrected as shown below:

On the Title page, item [22], "November 20, 1989" 1989" should be -- October 20, 1989 --.

On the Title page, item [56], the reference listed as:

"Work Holder and Alignment Device", Lanpdon et al., IBM Technical Disclosure Bulletin, vol. 5, No. 9, Feb. 1963, pp. 7-8" should be:

-- Work Holder and Alignment Device", Langdon et al., IBM Technical Disclosure Bulletin, vol. 5, No. 9, Feb. 1963, pp. 7-8 --.

Column 1, line 34, "Jaw" should be -- jaw --.

Column 2, line 35, "said" should be -- speed --.

Column 6, line 65, "he" should be -- be --.

Column 8, line 23, "oh" should be -- on --.

Column 8, line 60, before "observation" insert a beginning parenthesis -- ( --.

Column 9, line 12, after "plurality" delete the period ".".

Column 10, line 42, please change the quote (") before the word "sucked" to be a beginning quote.

UNITED STATES PATENT AND TRADEMARK OFFICE
CERTIFICATE OF CORRECTION

PATENT NO.  : 5,321,545
DATED       : June 14, 1994
INVENTOR(S) : Jean-Claude Bisconte It is certified that error appears in the above-identified patent and that said Letters Patent is hereby corrected as shown below:

Column 10, line 67, "maybe" should be -- may be --.

Column 11, line 37, "sad" should be -- said --.

Column 11, line 55, before "hole" insert -- said --.

Signed and Sealed this

First Day of November, 1994

Attest:

BRUCE LEHMAN

Attesting Officer

Commissioner of Patents and Trademarks